United States Patent [19]
Scheffel et al.

[11] 4,146,736
[45] Mar. 27, 1979

[54] PROCESS FOR THE MANUFACTURE OF ETHERS

[75] Inventors: Günter Scheffel, Burghausen, Salzach; Reinhold Obermeier, Mühldorf, both of Fed. Rep. of Germany

[73] Assignee: Hoechst Aktiengesellschaft, Frankfurt am Main, Fed. Rep. of Germany

[21] Appl. No.: 827,936

[22] Filed: Aug. 26, 1977

[30] Foreign Application Priority Data

Sep. 9, 1976 [DE] Fed. Rep. of Germany ....... 2640505

[51] Int. Cl.$^2$ ............................................. C07C 41/02
[52] U.S. Cl. .................................... 568/607; 568/608; 568/609; 568/610; 568/611; 568/613; 568/614; 252/364; 252/73; 252/184; 260/340.6

[58] Field of Search ............. 260/615 B, 613 B, 611 B

[56] References Cited

PUBLICATIONS

Latremouille et al., JACS, vol. 82 (1960) 120–124.
Merrall et al., Canadian Jour. Chem., vol. 38 (1960), 1967–1969.

*Primary Examiner*—Bernard Helfin
*Attorney, Agent, or Firm*—Connolly and Hutz

[57] ABSTRACT

Oxalkylene groups of oxacycloalkanes are inserted into chain-type ethers by reacting the latter with the oxacycloalkanes in the presence of Lewis acids. The ethers or ether mixtures obtained can be used for many purposes owing to their hydrophilic-hydrophobic character, for example as absorption and extraction agents, as solvents and as additives to hydraulic fluids.

3 Claims, No Drawings

PROCESS FOR THE MANUFACTURE OF ETHERS

The invention relates to a process for the manufacture of chain-type ethers, in which the oxalkylene groups of oxacycloalkanes are inserted into a compound of the general formula $$R_2-CH_2-(OR)_n-O-R_1 \qquad \text{I}$$

in which $R_1$ denotes an alkyl, aryl or aralkyl radical, $R_2$ represents hydrogen, chlorine or one of the meanings of $R_1$, n is an integer from 0 to 8 and OR represents identical or different oxalkylene groups of the formula $$-O-\overset{R_4}{\underset{|}{C}H}-(CH_2)_m-CH_2-$$

in which m is an integer from 0 to 4 and $R_4$ denotes hydrogen or, in the case of m = 0, also an alkyl radical having 1 to 4 C atoms, a chloromethyl radical or a phenyl radical.

The reaction of organic compounds which have active hydrogen in the molecule (that is to say mainly compounds with hydrogen bonded to oxygen, sulfur or nitrogen), for example alcohols or ether-alcohols, in the presence of oxonium salts, with oxacycloalkanes to give ether-alcohols or polyether-alcohols is known (compare DT-OS No. 2,300,248). For example, when ethyl alcohol and ethylene oxide are employed, the course of the reaction which takes place in this process is as follows:

$$C_2H_5-OH + n\,\underset{\underline{\hspace{1.5cm}}}{CH_2-CH_2-O} \xrightarrow{\text{Lewis acid}} \qquad (1)$$

$$C_2H_5-O-(CH_2-CH_2O)_n-H$$

The products obtained thus do not represent pure ether compounds but they are ether-alcohols or polyether-alcohols.

The incorporation of 1,2-epoxides, such as ethylene oxide, in the presence of boron trifluoride as the catalyst, into methyl-acetals, methyl-(β-alkoxy-methyl-)-acetals being formed, is also known (compare Houben-Weyl, "Methoden der organischen Chemie [Methods of Organic Chemistry]" 1965, volume VI/3, page 292), as is to be illustrated by the following equation (R being alkyl);

$$CH_3O-CH(R)-OCH_3 + \underset{\underline{\hspace{1.2cm}}}{CH_2-CH_2O} \longrightarrow \qquad (2)$$

$$CH_3O-CH(R)-O-CH_2-CH_2-OCH_3$$

Evidently, the fact that acetals are very readily dissociated in the presence of acids is utilized here (compare Houben-Weyl, "Methoden der organischen Chemie [Methods of Organic Chemistry]", 1965, volume VI/3, page 203 in conjunction with pages 272 and 273).

Moreover, the polymerization of oxacycloalkanes, such as ethylene oxide, trimethylene oxide, tetramethylene oxide (tetrahydrofurane) or cyclic ethers with a higher number of members, such as hexamethylene oxide (oxacycloheptane), individually or mixed with one another, with the aid of Lewis acids is known (compare DT-OS No. 1,495,209 and the journal "Angewandte Chemie" 72nd year, 1960/No. 24, page 927 to 1006). As stated in the journal, the reaction mechanism of this polymerization is essentially based on the fact that, under the action of Lewis acids, the ring structure of the oxacycloalkanes is split and one oxalkylene group after another can thus undergo and addition reaction.

Thus whilst, on the one hand, using cationic catalysts, the insertion of oxacycloalkanes in the form of oxalkylene groups into acetals and into organic compounds having active hydrogen, that is to say hydrogen which is reactive towards alkylene oxides (the term oxalkylation is usual for this reaction) and, on the other hand, the polymerization of oxacycloalkanes with one another are known, the insertion of oxacycloalkanes in the form of oxalkylene groups into acyclic (chain-type) ethers according to the formula I has not hitherto been described.

Compounds of this type, for example methyl ethers of phenols, aliphatic alcohols and alkylglycols, are in themselves known. According to the state of the art (compare Ullmann's "Encyklopädie der technischen Chemie [Encyclopedia of Industrial Chemistry]", 1974, volume 8, page 148, left-hand column), they are manufactured preferably by reacting an alcohol with an oxacycloalkane according to the reaction (1) shown above, converting the resulting compound to the glycolate by means of alkali and converting the glycolate to the diether compound by means of alkyl halide or dialkyl sulfate. The following equation is meant to illustrate the three-stage reaction on which the process is based, using the example of methanol, ethylene oxide, sodium hydroxide solution and methyl chloride:

$$CH_3OH + 2\,\underset{\underline{\hspace{1.5cm}}}{CH_2-CH_2-O} \longrightarrow$$

$$CH_3OCH_2CH_2OCH_2CH_2OH \qquad (3)$$

$$CH_3OCH_2CH_2OCH_2CH_2OH + NaOH \xrightarrow{-H_2O}$$
$$CH_3OCH_2CH_2OCH_2CH_2ONa \qquad (4)$$

$$CH_3OCH_2CH_2OCH_2CH_2ONa + CH_3Cl \xrightarrow{-NaCl}$$
$$CH_3OCH_2CH_2OCH_2CH_2OCH_3 \qquad (5)$$

This process, which has already been known for a long time, for the industrial manufacture of such ethers has serious disadvantages:

A low space-time yield since the dehydration of the glycolate takes a long time; high material costs, in particular due to the relatively expensive starting alcohols; extensive environmental pollution due to the NaCl obtained; in addition to the pure ethers, mono-ethers, that is to say ether-alcohols, the separation of which from the diethers is relatively difficult and industrially expensive, are also still present in the product obtained.

In recent years, further processes for the manufacture of the ethers under consideration have been developed (compare Ullmann's "Encyklopädie der technischen Chemie [Encyclopedia of Industrial Chemistry]", 1974, volume 8, page 205). One manufacturing method uses methanol, ethylene chloride and Mg hydroxide or Zn hydroxide as the starting materials. In this case, twice molar amounts of salt are evidently produced as the result of etherification on both sides. In the second method, ethylene and methanol are the starting materials. For this purpose, a catalytic oxidation process by means of iodine is necessary, and this process requires a large technical effort and gives large proportions of unutilizable by-products. In view of the disadvantages, it has also been suggested to manufacture dimethyl glycol ethers by converting the corresponding methylglycols by means of formaldehyde into formals and to split the latter by hydrogenolysis to give the desired dimethyl glycol ether, equimolar amounts of the monomethyl glycol ether employed being recovered (DT-OS No. 2,434,057). Although substantial progress is achieved by this process, the forced recycle of 50% of the raw material impairs the space-time yield.

The many different efforts to manufacture chain-type (true) ethers also underline the market demand for the latter. It is thus the object of the invention to indicate a process for the manufacture of ethers of this type, which is economical and causes low environmental pollution.

This object is achieved by reacting the compounds according to the formula I, in the presence of Lewis acids, with oxacycloalkanes of the general formula

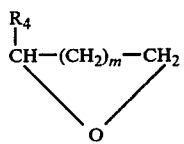

II in which $R_4$ and m have the meaning mentioned above, 3- membered to 4-membered oxacycloalkanes also being present in the case of a reaction with oxacycloalkanes having more than 4 members.

Since, without doubt, there has been, for a long time, an industrial demand for an economical and simple process for the manufacture of the ethers under consideration, it is very surprising that nobody has yet discovered the process according to the invention, the more so since the considerable disadvantages of the known processes for an industrial production of these ethers have been known for a long time. It was therefore not to be expected that a reaction of oxacycloalkanes is also possible with the chain-type ethers, according to the formula I, which are known to be very stable, in such a way that both the ether and the oxacycloalkane break up at the oxygen-carbon bond and the oxacycloalkane is inserted as a chain member into the ether.

The known scission of the C-O bond in the reaction of ethers with Lewis acids also gives no indication in the direction of the present invention (compare Houben-Weyl, "Methoden der organischen Chemie [Methods of Organic Chemistry]", 1965, volume VI/3, page 156). This is so because in all these reactions the ether compounds as such are destroyed, two new compounds being formed into each of which one part of the reactant is incorporated. The two reactions which follow are meant to illustrate this:

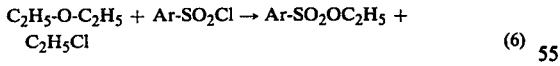

(6)

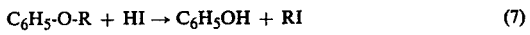

(7)

(compare Weygandt-Hilgetag, "Org. chem. Experimentierkunst [The Art of Experimenting in Organic Chemistry]", 1970, page 402). By contrast, in the process according to the invention oxalkylenes are inserted, the terminal members being retained, and another ether results from ethers.

Numerous papers, in particular also those by Meerwein, the founder of the oxonium salt theory (compare the treatise on ethers and acetals in the cited reference book by Houben-Weyl) thus dealt with the compounds (starting materials) on which the process according to the invention is based, but the combination of starting materials, characteristic of the process according to the invention, was not discovered.

Thus, it must be stated that the known reactions between diethers or monoethers, epoxides and Lewis acids would rather deter those skilled in the art from the present invention and that, in spite of an incontestable demand for an industrially simple method for the manufacture of chain-type (true) ethers, nobody has yet discovered the particularly advantageous process according to the invention, that is to say it was not obvious.

Suitable compounds (starting ethers) according to the formula I are preferably those in which $R_1$ denotes a straight-chain or branched, preferably straight-chain, alkyl radical having 1 to 12 C atoms, an (unsubstituted) phenyl radical, a phenyl radical carrying 1 to 2 chlorine atoms, a phenyl radical carrying a straight-chain or branched, preferably straight-chain, alkyl or alkoxy radical having 1 to 4 C atoms, a phenyl radical carrying a straight-chain or branched, preferably straight-chain, alkyl radical which has 1 to 4 C atoms and is substituted by 1 to 2 chlorine atoms, or an aralkyl radical composed of an (unsubstituted) phenyl radical and a straight-chain or branched, preferably straight-chain, alkyl radical having 1 to 4 C atoms, $R_2$ is a hydrogen atom or chlorine atom or has one of the meanings of $R_1$ (that is to say, $R_1$ and $R_2$ in the formula I can be identical or different), n is an integer from 0 to 8 and OR denotes one or more, identical or different oxalkylene groups (the total sum of n being 0 to 8) from the following series:

—OCH$_2$CH$_2$—

—OCH$_2$CH$_2$CH$_2$—

—OCH$_2$CH$_2$CH$_2$CH$_2$—

—OCH$_2$CH$_2$CH$_2$CH$_2$CH$_2$—

—OCH$_2$CH$_2$CH$_2$CH$_2$CH$_2$CH$_2$—

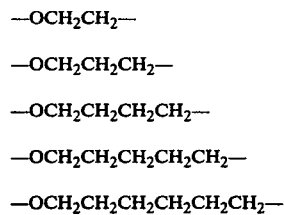

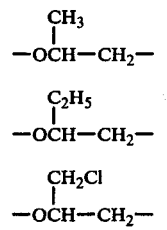

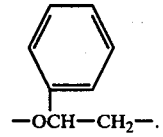

$R_1$ especially denotes a straigh-chain alkyl radical having 1 to 4 C atoms, a phenyl radical, a phenyl radical having 1 to 2 chlorine atoms or a benzyl radical and OR especially represents one of the following oxalkylene groups:

—OCH$_2$—CH$_2$—

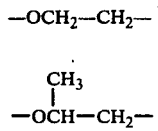

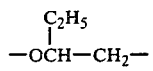

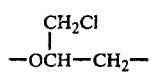

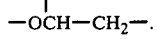

The following may be mentioned as examples of advantageous starting compounds: ethers having identical or different alkyl radicals, such as dimethyl ether, diethyl ether, dipropyl ether, di-isopropyl ether, di-butyl ether, methyl ethyl ether, methyl propyl ether, chloromethyl propyl ether, methyl butyl ether, methyl octyl ether, methyl dodecyl ether, methyl benzyl ether, phenylpropyl methyl ether, 3-chlorophenyl methyl ether, phenyl benzyl ether, 1,2-propylene glycol dimethyl ether, 1,2-propylene glycol diethyl ether and dimethylhydroquinone; the reaction products of these ethers according to the invention, such as, for example, the methyl alkyl ethers of monoethylene glycol, diethylene glycol, triethylene glycol or tetraethylene glycol, and analogous methyl alkyl ethers which, completely or partially, contain trimethylene oxide, tetrahydrofurane or hexamethylene oxide as chain members, for example $H_3C$-O-$CH_2$-$CH_2$-O-$(CH_2)_4$-O-$CH_3$ and $H_3C$-(O-$CH_2$-$CH_2$-$CH_2)_2$-(O-$CH_2$-$CH_2)_2$-O-$C_3H_7$ (the sequences of the chain members are to be assumed to have a statistical distribution). If the starting ether is a polyfunctional ether in the sense of the invention (that is to say if it contains, for example, more than one $R_2$-$CH_2$-O- group per molecule), the insertion according to the invention is possible at several points.

The Lewis acids which are to be employed in the process according to the invention can differ very widely in their composition and their structure. Lewis acids (individually or as a mixture) in the form of metal halides and metalloid halides, such as $BF_3$, $FeCl_3$, $SnCl_4$ or $PF_5$, in the form of hydrogen acids, preferably HF, in the form of aluminum hydrosilicates, such as montmorillonite, and in the form of coordination complexes of metal halides or metalloid halides with organic compounds, such as halogenoalkyls, ethers, acid chlorides, acid esters or acid anhydrides are preferably suitable. Trialkyloxonium salt complexes having identical or different alkyl groups, analogous acylium salt complexes and unsaturated tertiary oxonium salts, that is to say the tertiary carboxonium salts, are also preferably suitable. Lewis acids of this type are described in detail in the journal "Angewandte Chemie" 72nd year/1960- /No. 24, page 927 to 1006.

Different Lewis acids of this type are employed as an alternative in Table I of Example 3. It can be seen from the indicated results that the distribution spectra obtained display differences which depend on the type of catalyst system selected.

Ethylene oxide, 1,2-propylene oxide, 1,2-butylene oxide, trimethylene oxide, tetramethylene oxide, pentamethylene oxide, hexamethylene oxide, epichlorohydrin and styrene oxide, individually or mixed with one another, are preferably suitable as the oxacycloalkanes; ethylene oxide, 1,2-propylene oxide, 1,2-butylene oxide, tetramethylene oxide, epichlorohydrin and styrene oxide, individually or mixed with one another, are preferentially employed.

If an oxacycloalkane with more than 4 members is employed, proportions of 3-membered to 4-membered oxacyclalkanes, are added to avoid a chain polymerisation which the oxacycloalkanes with more than 4 members tend to undergo (compare DT-OS No. 1,495,209). These proportions amount to at least 5% by weight, preferably 10 to 90% by weight and in particular 50 to 90% by weight, relative to the total mixture (sum of the oxacycloalkanes employed). At the same time, this gives products of a more pronounced hydrophilic character.

The process according to the invention can be carried out continuously or discontinuously, and the starting ethers and oxacycloalkanes are subjected to the reaction without pressure or under pressure, depending on the vapor pressures being established.

Since the reaction according to the invention takes place exothermically, it is advantageous to use a reaction apparatus which permits a rapid removal of the heat of reaction. This can be achieved by indirect heat exchange by means of a cooler or, if appropriate, by boiling off and recondensing a reactant or solvent. Thus, the apparatus appropriately consists of a reaction vessel which is fitted with a stirring system and a double jacket as well as a reflux condenser if appropriate. If the reaction is carried out discontinuously, the starting product and the catalyst are initially introduced and the oxacycloalkane is metered in, in particular at the rate at which the heat of reaction can be removed, the mixture being stirred during the conversion (reaction).

In the simplest case of industrial production, a pressure-resistant reaction kettle is chosen which is charged discontinuously. An industrially better control of the reaction is achieved if the kettle contents are circulated via a high-performance cooler arranged externally. After all the oxacycloalkane has been metered in, the reaction mixture is advantageously kept at the same temperature or, if appropriate, at a somewhat higher temperature for same further period, about 15 minutes up to one hour, whilst stirring — in order to complete the reaction — and is subsequently cooled. Since the catalysts still exert an activity on the relative composition of the components in the distribution spectrum, even after the reaction has ended, it proves advantageous to render the catalyst harmless after completion of the reaction. This is suitably accomplished by the addition of bases with which the Lewis acid is neutralized. Examples of suitable bases are inorganic bases, such as alkali metal carbonates, alkali metal bicarbonates, alkaline earth metal carbonates and alkaline earth metal oxides, or organic bases, such as triethanolamine. The addition of solid alkali metal carbonates or alkali metal bicarbonates has proved particularly advantageous.

The continuous reaction in which the starting components and the reaction mixture are continuously fed in or withdrawn respectively, is advantageously carried out in a double-jacket tube since, in that case, it is also possible, in a simple manner, to maintain short residence times. A continuous reaction procedure is indicated especially if it is necessary to recirculate low-molecular fractions in order to maximize the build-up of reaction products of a defined chain length within a homologous series. For example, the co-current reactor described in German Pat. No. 2,016,323 is suitable as a double-jacket reactor.

Appropriately, the reaction according to the invention is carried out with the exclusion of compounds having active hydrogen, such as alcohols, amines, mercaptans, glycols or water, since otherwise by-products are formed which are not desirable for the purpose of the invention. The reaction can be carried out in bulk or in the presence of inert solvents, such as, for example, $\beta,\beta'$-dichlorodiethyl ether, dichloromethane, nitromethane, chlorobenzene or ethyl acetoacetate.

In the case of ethylene oxide being employed as the oxacycloalkane in the process according to the invention, dioxane is unavoidably formed as a by-product, and the proportion of dioxane in the reaction mixture increases as the molecular weight of the reaction product rises. To repress this undesired side reaction, it has proved advantageous to avoid relatively high concentrations of oxide, for example by using inert solvents. A more than proportional reduction of the build-up of dioxane can also be achieved by employing, instead of pure ethylene oxide, a mixture of ethylene oxide and tetrahydrofurane with 5 to 40% by weight, preferably 10 to 25% by weight, of tetrahydrofurane, relative to the total mixture. In that case products with statistically incorporated tetrahydrofurane, which only insignificantly alters the properties of the homologous series of the dimethyl glycol ethers, are obtained.

The reaction rate is dependent on the concentration of the Lewis acid, on the reaction temperature, on the type of starting substance (starting ether) and on the type of oxacycloalkane. The amount of Lewis acid is in general 0.01 mole % to 10 mole %, relative to the starting substance, preferably 0.05 mole % to 2 mole %. The reaction temperature is 0 to 120° C., preferably 20 to 90° C. and in particular 40 to 70° C. The reaction rate decreases with the presence of a phenyl radical as $R_1$ in the compounds of the formula I (starting substance). Amongst the oxacycloalkanes, ethylene oxide, epichlorohydrin and trimethylene oxide are particularly readily inserted. The composition of the end product can be regulated by the ratio of the amounts of oxacycloalkane and starting ether employed. For example, if it is desired to obtain an ether according to formula I with n = 2, a corresponding ether with n = 1 is preferably used as the starting material. In order to render the yield of ether with n = 2 as high as possible, a high ratio of starting ether to oxacycloalkane, as a rule from 2 : 1 to 50 : 1, preferably from 2 : 1 to 10 : 1, will also be selected; in this way the formation of higher homologous ethers is repressed. If, on the other hand, it is intended to manufacture, for example, a mixture of homologs of a higher chain length with a desired distribution of the individual ethers in the mixture (with a view to fields of application, for which a separation into individual ether compounds is not required), the lower members of the series of homologs will together by recycled again into the reaction. The quoted measures are generally customary in the chemical industry for shifting chemical reactions into a desired direction.

The process according to the invention overcomes the disadvantages inherent in the known processes. It is a one-stage process which can be carried out in an industrially very simple manner (mild reaction conditions). The starting ethers are largely industrial low-cost compounds and some of them are extremely cheap. Thus, for example, dimethyl ether, which can preferably be employed as the starting ether, is a by-product of the methanol synthesis, and industrial fields where it can be employed are still being sought (compare Ullmann, 1974, volume 8, page 148).

On the one hand, the present invention meets the industrial demand, which has existed for a long time, for a process, which is very much more economical as compared with the state of the art, for the manufacture of chain-type ethers, in some cases even using a waste product, and on the other hand, the process according to the invention gives very pure diethers which are of great industrial importance since they can be utilized in many different ways — individually or as a mixture.

Thus, dialkyl ethers of $\alpha, \omega$-alkanediols, such as dimethyl glycol ether or 1,4-butylene glycol dimethyl ether, possess interesting technological properties which are based specifically on their hydrophilic/hydrophobic character: they are miscible with many organic solvents and, depending on the choice of the non-terminal oxalkgylene groups and the terminal groups, are water-soluble to different degrees without, however, containing the typical hydrophilic functional groups having active hydrogen, such as, for example, hydroxyl groups or amino groups. In this way, they represent selective absorption agents and extraction agents as well as inert solubilizers, which can be employed with excellent effect, optionally also in the form of mixtures, in hydraulic fluids and also, due to their character as Lewis bases, as absorption agents for acid gases, in particular for refinery gases and natural gases, and furthermore as solvents for lacquers or also in chemical reactions, such as, for example, the Grignard reaction. The point which especially distinguishes the process according to the invention is that these diverse properties can, in a manner of speaking, be obtained tailor-made.

It follows from the importance, already mentioned, of the ethers under consideration and their versatility in use that not only an individual ether alone but also mixtures which result as a homologous series when the starting ethers and oxacycloalkanes are reacted in a defined ratio are of industrial importance. This applies particularly to homologs with longer chains which, on the one hand, can no longer be separated by distillation but are, on the other hand, so similar to one another that they can be employed as mixtures without any disadvantage.

The invention is explained in the following test with the aid of examples.

EXAMPLE 1

50 moles (2,300 g) of dimethyl ether and 0.1 mole (10 ml) of boron fluoride dimethyl etherate are initially introduced into a 5 liter stirred autoclave which has been flushed with nitrogen and evacuated. 10 moles (440 g) of ethylene oxide are metered in at 55° C. in the course of one hour, whilst stirring. After the pressure has fallen from 12 bars to 10 bars, stirring at 55° C. is continued for a further half hour.

The residual content of ethylene oxide in the reaction solution is <0.1%. After the excess dimethyl ether (1,928 g) has been stripped off, a residue of about 800 g remains which gives the following analysis by gas chromatography: 2.8% of dimethyl ether, 65.2% of dimethylglycol, 8.2% of dioxane, 12.6% of dimethyldiglycol, 5.9% of dimethyltriglycol, 2.5% of dimethyltetraglycol and 1.1% of dimethylphentaglycol. The mixture is neutralized with $NaHCO_3$ and worked up by distillation, the analysis by gas chromatography being confirmed by gravimetric analysis.

A separation column with Chromosorb and 5% of polyethylene glycol 20,000 is used for the analysis by gas chromatography (GC analysis).

EXAMPLE 2

16 moles (1,440 g) of dimethylglycol and 0.01 mole (1 ml) of boron fluoride dimethyl etherate as the catalyst are intitially introduced into a 2 liter stirred flask fitted with a reflux condenser and a gas inlet tube. 4 moles (176 g) of ethylene oxide are passed in as a gas at 50° C. in the course of one hour, whilst stirring. During this addition cooling is necessary since the reaction is strongly exothermic; escaping ethylene oxide is recondensed by means of a reflux condenser which is charged with a mixture of solid carbon dioxide and ethanol. After the addition of ethylene oxide has ended, the mixture is further stirred at 50° C. for another 15 minutes and is subsequently neutralized with 1 g of solid sodium bicarbonate.

The residual content of ethylene oxide in the reaction solution is <0.1%. The reaction mixture is investigated by gas chromatography and, after fractionation, by gravimetric analysis. The result is: 1.25% of dimethyl ether, 74.35% of dimethylglycol, 1.95% of dioxane, 16.75% of dimethyldiglycol, 4.1% of dimethyltriglycol, 1.2% of dimethyltetraglycol and 0.4% of dimethylpentaglycol.

EXAMPLE 3

A comparative series with various catalysts according to Table 1 is carried out as follows:

1 mole (90 g) of dimethylglycol and the particular amount of catalyst indicated in Table 1 (in mole %, relative to ethylene oxide) are initially introduced into a 0.5 liter stirred flask fitted with a reflux condenser and gas inlet tube.

0.5 mole (22 g) of ethylene oxide are then passed in as a gas at 50° C. Subsequently the mixture is further stirred at 50° C. for another 15 minutes and the reaction mixture is investigated by gas chromatography; the analytical result is also listed in Table 1.

Table 1

| Catalyst | Catalyst concentration (mole % relative to ethylene oxide) | Ethylene oxide | Dimethyl ether | Dimethyl-glycol | Dioxane | Dimethyl-diglycol | Dimethyl-triglycol | Dimethyl-tetraglycol | Dimethyl-pentaglycol | Dimethyl-hexaglycol |
|---|---|---|---|---|---|---|---|---|---|---|
| $BF_3$ | 0.5 | — | 2.8 | 58.7 | 7.1 | 21.0 | 6.5 | 2.5 | 0.8 | 0.3 |
| $PF_5$ | 0.5 | — | 2.2 | 62.5 | 7.7 | 15.5 | 6.3 | 3.7 | 1.7 | 0.7 |
| $SbF_5$ | 0.5 | — | 2.2 | 62.0 | 6.8 | 17.0 | 6.3 | 3.5 | 1.7 | 0.7 |
| $JF_5$ | 0.5 | — | 2.3 | 57.5 | 7.0 | 20.1 | 6.5 | 3.8 | 1.8 | 0.7 |
| $SiF_4$ | 0.5 | — | 2.4 | 58.0 | 6.8 | 19.5 | 6.8 | 3.7 | 1.7 | 0.8 |
| $HBF_4$ | 0.5 | — | 2.0 | 62.4 | 5.5 | 18.5 | 7.3 | 3.2 | 1.5 | — |
| HF | 1.0 | — | 0.8 | 64.7 | 4.5 | 10.7 | 6.6 | 2.8 | 1.3 | — |
| $HF + B_2O_3$ | 0.5 | — | 2.0 | 59.0 | 6.0 | 18.5 | 7.0 | 3.6 | 1.5 | 0.6 |
| $HF + B(OR)_3$ | 0.5 | — | 1.0 | 64.7 | 3.7 | 16.3 | 10.2 | 3.3 | 1.6 | 0.7 |
| $HF + BCl_3$ | 0.5 | — | 0.7 | 68.6 | 3.0 | 15.0 | 6.3 | 3.1 | 1.5 | — |
| $BF_3 + (CH_3)_2SO_4$ | 0.5 | — | 6.80 | 62.37 | 6.80 | 16.63 | 4.78 | 2.15 | — | — |
| $BF_3 + CH_3Cl$ | 0.5 | — | 6.82 | 63.48 | 5.30 | 17.99 | 4.10 | 2.35 | 1.2 | — |
| $FSO_3H + BCl_3$ | 0.5 | 4.0 | 1.1 | 64.4 | 4.3 | 18.6 | 7.3 | 3.1 | 1.0 | 0.6 |
| $FSO_3H + Si(OCH_3)_4$ | 1.0 | — | 1.0 | 70.7 | 2.6 | 13.3 | 4.8 | 2.2 | 1.5 | 0.2 |
| $FSO_3H + B(OR)_3$ | 0.5 | — | 2.4 | 57.3 | 6.6 | 20.2 | 7.1 | 3.6 | 0.9 | — |
| $FSO_3CH_3 + B(OR)_3$ | 0.5 | — | 1.4 | 66.4 | 4.0 | 18.3 | 5.6 | 2.4 | 0.7 | — |
| $FeCl_3 + PCl_5$ | 1.0 | — | 1.5 | 65.5 | 2.1 | 14.1 | 5.0 | 2.1 | 1.1 | — |
| $FeCl_3 + POCl_3$ | 1.0 | — | 2.0 | 64.2 | 3.7 | 17.9 | 6.4 | 3.0 | 1.2 | — |
| $FeCl_3 + S_2Cl_2$ | 1.0 | — | 1.2 | 64.1 | 3.4 | 17.2 | 6.7 | 3.0 | — | — |
| $FeCl_3 + AlCl_3$ | 1.0 | — | 0.7 | 74.8 | 0.4 | 7.9 | 2.0 | 0.6 | 1.3 | — |
| $FeF_3 + HF$ | 1.0 | — | 1.0 | 65.0 | 6.0 | 16.0 | 6.5 | 2.8 | 1.3 | — |
| | 0.5 | — | 2.3 | 59.9 | 6.9 | 20.9 | 6.4 | 2.4 | 0.9 | — |
| $\left[\begin{array}{c}CH_3OCH_3\\CH_3\end{array}\right]^+ BF_4^-$ | 1.0 | — | 2.0 | 62.0 | 6.7 | 17.0 | 6.5 | 3.7 | 1.7 | 0.8 |
| $\left[HC\begin{array}{c}OCH_3\\OCH_3\end{array}\right]^+ SbF_6^-$ | 1.0 | — | 1.6 | 63.2 | 5.0 | 18.0 | 6.2 | 2.5 | 0.7 | — |
| $\left[NO_2-\!\!\bigcirc\!\!-N \equiv N\right]^+ BF_4^-$ | 1.0 | — | 0.8 | 62.3 | 5.8 | 20.4 | 6.3 | 2.5 | 0.9 | — |
| $\left[C(\bigcirc)_3\right]^+ BF_4^-$ | 1.0 | 5.2 | 2.0 | 64.0 | 4.7 | 16.7 | 4.9 | 1.6 | 0.5 | — |
| $\left[C(\bigcirc)_3\right]^+ PF_6^-$ | | | | | | | | | | |

EXAMPLE 4

1 mole (104 g) of dimethylpropylene glycol and 0.005 mole of boron fluoride dimethyl etherate are initially introduced into a 0.5 liter stirred flask fitted with a reflux condenser.

0.5 mole (22 g) of ethylene oxide are then passed in as a gas in the course of 30 minutes, whilst stirring. During this procedure the temperature is held at 50° C. After the introduction of gas has ended the temperature is held at 50° C. for about a further 30 minutes and subsequently the mixture is analyzed. The analysis by gas chromatography gives:

84.3% of dimethylpropylene glycol $CH_3$-O-$CH(CH_3)$-$CH_2$-O-$CH_3$, 2.03% of methylglycol, 3.87% of $CH_3$-O-$CH(CH_3)$-$CH_2$-O($CH_2CH_2O$)$_1CH_3$, 2.98% of $CH_3$-O-$C(CH_3)CH_2$-O($CH_2O$)$_2$-$CH_3$, 0.84% of x (not identified) and 0.68% of $CH_3$-O-$C(CH_3)CH_2$-O($CH_2CH_2O$)$_3$-$CH_3$.

The sequence of the oxalkylene groups is statistical.

EXAMPLE 5

4.3 moles of methyl ethyl ether and 0.03 mole of boron fluoride dimethyl etherate are initially introduced into an evacuated 1 liter stirred autoclave. After the autoclave has been heated up to 55° C., 1 mole of ethylene oxide is metered in. After 90 minutes the pressure is released. The reaction mixture is treated with 3 g of sodium bicarbonate and freed from excess methyl ethyl ether. A residue of 57 g results.

The analysis by gas chromatography gives 14.3% of dimethylglycol, 32.0% of methylethylglycol, 7.5% of diethylglycol, 7.0% of dioxane, 5.8% of dimethyldiglycol, 10.3% of methylethyldiglycol, 4% of diethyldiglycol, 10.5% as the sum of homologous dialkyltriglycols, 4.8% of dialkyltetraglycols and 3.8% of dialkylpentaglycols.

EXAMPLE 6

1 mole of methyl n-propyl ether and 0.01 mole of boron fluoride dimethyl etherate are initially introduced into a 0.5 liter stirred flask fitted with a reflux condenser. 0.5 mole of ethylene oxide in the gaseous form are introduced at a temperature of 23° C. The reflux condenser is operated at −50° C.

The reaction product shows the following analysis: 75.7% of methyl propyl ether, 1.5% of dimethylglycol, 3,5% of methylpropylglycol, 1.4% of dipropylglycol, 8.5% of dioxane, 0.7% of dimethyldiglycol, 2.1% of methylpropyldiglycol, 1.0% of dipropyldiglycol, 0.5% of dimethyltriglycol, 1.6% of methylpropyltriglycol, 0.7% of dipropyltriglycol, 0.4% of dimethyltetraglycol, 1.0% of methylpropyltetraglycol, 0.4% of dipropyltetraglycol, 0.3% of dimethylpentaglycol, 0.5% of methylpropylpentaglycol and 0.2% of dipropylpentaglycol.

EXAMPLE 7

1 mole of methyl benzyl ether and 0.01 mole of boron fluoride dimethyl etherate are initially introduced into an apparatus according to Example 6. 0.5 mole of ethylene oxide is passed in as a gas at a temperature of 50° C. A sample withdrawn after about 1 hour shows the following analysis: 0.85% of dimethylglycol, 1.3% of dioxane, 76.5% of methyl benzyl ether, 14.4% of methylbenzylglycol, 5.2% of methylbenzyldiglycol and 1.7% of methylbenzyltriglycol.

EXAMPLE 8

1 mole (148 g) of 3-phenylpropyl methyl ether, together with 0.005 mole of boron fluoride dimethyl etherate, is initially introduced into a 0.5 liter stirred flask fitted with a reflux condenser.

0.5 mole (22 g) of ethylene oxide is then added as a gas in the course of 30 minutes, whilst stirring. The temperature is held at 50° C. by means of a water bath. After the introduction of the gas has ended, the temperature is held at 50° C. for about a further 30 minutes by means of warm water and subsequently the mixture is analyzed.

The analysis by gas chromatography gives: 2.0% of dimethylglycol, 6.6% of dioxane, 78.8% of phenylpropyl methyl ether, 6.7% of the reaction product with one mole of ethylene oxide per mole, 3.5% of the reaction product with two moles of ethylene oxide and 0.5% of the reaction product with three moles of ethylene oxide.

EXAMPLE 9

240 kg of methylene chloride and 1.2 kg of boron fluoride dimethyl etherate are initially introduced into a 1.5 m$^3$ stirred kettle made of steel and additionally equipped with controllable water cooling equipment and with a pressure lock of 150 liters capacity.

92 kg of liquid dimethyl ether are injected via the lock. On heating to 45° C., a pressure of 3.8 bars is established.

In the course of one hour, 44 kg of ethylene oxide are metered in via the pressure lock. The temperature is held at 50° C. Stirring at 50° C. is continued for a further 30 minutes. The residual content of ethylene oxide in the reaction mixture is <0.1%.

The unconverted dimethyl ether mixed with methylene chloride is extracted via the let-down line and the mixture is flushed with nitrogen and neutralized with 1.5 kg of sodium carbonate.

The analysis shows the following constituents by weight: 1.6% of dimethyl ether, 72.0% of $CH_2Cl_2$, 16% of dimethylglycol, 1.7% of dioxane, 6.0% of dimethyldiglycol, 1.7% of dimethyltriglycol, 0.5% of dimethyltetraglycol and 0.2% of dimethylpentaglycol.

The results from gas chromatography are qualitatively and quantitatively confirmed by the fractions obtained on distillation.

EXAMPLE 10

After a 1 liter stirred autoclave has been evacuated, 4 moles (184 g) of dimethyl ether and 0.03 mole of boron fluoride dimethyl etherate are introduced and the mixture is preheated to 55° C. In the course of half an hour, 2.5 moles (231 g) of epichlorohydrin are metered in and the heat of reaction is removed at 55° C. The pressure falls from 12 bars to 5 bars in the course of 3 hours at 55° C. The reaction product is treated with 3 g of sodium bicarbonate and freed from excess dimethyl ether by evaporation. The residue shows the following analysis by gas chromatography: 75% of chloromethylethylene glycol dimethyl ether, 15% of di-(chloromethylethylene glycol) dimethyl ether and 5% of tri-(chloromethylethylene glycol) dimethyl ether.

EXAMPLE 11

1 mole (122 g) of methyl benzyl ether and 0.005 mole of boron fluoride dimethyl etherate are initially introduced into a 0.5 liter stirred flask fitted with a reflux condenser.

Subsequently 0.5 mole (46.2 g) of epichlorohydrin is added dropwise in the course of half an hour, whilst stirring. During this procedure, the temperature is held at 50° C. by means of cooling water. After the addition of epichlorohydrin has ended, the mixture is held at 50° C. for a further 15 minutes and then analyzed.

The analysis by gas chromatography shows: 54.5% of methyl benzyl ether and 44.5% of the reaction product with 1 mole of epichlorohydrin.

EXAMPLE 12

1 mole (150 g) of phenylpropyl methyl ether and 0.01 mole of boron fluoride dimethyl etherate are initially introduced into a 0.5 liter stirred flask fitted with a reflux condenser. 0.5 mole (46.2 g) of epichlorohydrin is then added dropwise at 70° C. in the course of half an hour, whilst stirring. After the addition of epichlorohydrin has ended, the mixture is stirred at 70° C. for a further 5 minutes and then analyzed.

The analysis by gas chromatography shows: 11.6% of epichlorohydrin, 65.2% of phenylpropyl methyl ether and 20.5% of the reaction product of 1 mole of phenylpropyl methyl ether with 1 mole of epichlorohydrin.

EXAMPLE 13

0.13 mole of dimethyl ether, 0.002 mole of boron fluoride dimethyl etherate and 0.034 mole of trimethylene oxide are sealed into a 20 ml pressure tube. After a period of 60 minutes at 50° C. and occasional shaking, the reaction mixture is freed from excess dimethyl ether and analyzed as follows: 26.0% of 1,3-propylene glycol dimethyl ether, 23.8% of dipropylene glycol dimethyl ether, 16.3% of tripropylene glycol dimethyl ether, 15.4% of tetrapropylene glycol dimethyl ether, 11.4% of pentapropylene glycol dimethyl ether and 7.1% of hexapropylene glycol dimethyl ether.

EXAMPLE 14

2.5 kmoles (225 kg) of dimethylglycol and 1 liter of boron fluoride dimethyl etherate are initially introduced into an evacuated 1 m$^3$ stirred autoclave. The autoclave is heated to 45° C. in the course of one hour. A mixture of 2.5 kmoles (110 kg) of ethylene oxide and 0.625 kmole (45 kg) of tetrahydrofurane is allowed to run in in the course of about 2 hours. After a final reaction period of half an hour, the residual content of ethylene oxide is <0.5%. A sample of the reaction product is investigated by gas chromatography, the following composition being shown:
 1.8% $C_4H_8O$ tetrahydrofurane
 29.5% $CH_3O(C_2H_4O)$-$CH_3$ dimethylglycol
 5.4% $(C_2H_4O)_2$ dioxane
 12.0% $CH_3O(C_2H_4O)_2$-$CH_3$ dimethyldiglycol
 1.3% $CH_3$-O-$(C_2H_4O)$-$(C_4H_8O)$-$CH_3$
 9.2% $CH_3$-O-$(C_2H_4O)_3$-$CH_3$ dimethyltriglycol
 12.5% $CH_3$-O-$(C_2H_4O)_2$-$(C_4H_8O)$-$CH_3$
 5.5% $CH_3$-O-$(C_2H_4O)_4$-$CH_3$ dimethyltetraglycol
 10.8% $CH_3$-O$(C_2H_4O)_4$-$C_4H_8O)$-$CH_3$
 1.9% $CH_3$-O-$(C_2H_4O)_5$-$CH_3$ dimethylpentaglycol
 8.9% $CH_3$-O-$(C_2H_4O)_4$-$(C_4H_8O)$-$CH_3$
 1.2% $CH_3$-O-$(C_2H_4O)_6$-$CH_3$ dimethylhexaglycol The present mixture is neutralized with 1 kg of sodium bicarbonate. A light ends fraction up to a boiling point of 103° C. at 20 mm Hg is separated off by means of a 15-tray column at a reflux ratio of 1:1 and this fraction is set aside as the starting ether for re-use. The residue of about 50% by weight has the following analysis:
 18.4% $CH_3$-O-$(C_2H_4O)_3$-$CH_3$ dimethyltriglycol
 25.0% $CH_3$-O-$(C_2H_4O)_2$-$(C_4H_8O)$-$CH_3$
 11.0% $CH_3$-O-$(C_2H_4O)_4$-$CH_3$ dimethyltetraglycol
 21.6% $CH_3$-O-$(C_2H_4O)_3$-$(C_4H_8O)$-$CH_3$
 3.8% $CH_3$-O-$(C_2H_4O)_5$-$CH_3$ dimethylpentaglycol
 17.9% $CH_3$-O-$(C_2H_4O)_4$-$(C_4H_8O)$-$CH_3$
 2.3% $CH_3$-O-$(C_2H_4O)_6$-$CH_3$ dimethylhexaglycol This mixture is miscible with water in any proportions and possesses excellent properties as a selective absorpotion agent for $H_2S$ and $SO_2$ is gases.

EXAMPLE 15

0.5 mole of hexamethylene oxide, 0.03 mole of boron fluoride dimethyl etherate and 5 moles of dimethyl ether are initially introduced into an evacuated 1 liter stirred autoclave.

The mixture is warmed to 55° C. without a reaction starting. 2 moles of ethylene oxide are then injected in the course of a period of 45 minutes. The heat of reaction generated is removed whilst maintaining the temperature of 55° C. The reaction is allowed to proceed further for half an hour. After evaporating the excess dimethyl ether, the residue has the following analysis:
 36.7% $CH_3$-$(OC_2H_4)$-$OCH_3$ dimethylglycol
 10.2% $(C_2H_4O)_2$ dioxane
 9.4% $C_6H_{12}O$ hexamethylene oxide
 15.0% $CH_3$-$(OC_2H_4)_2$-$OCH_3$ dimethyldiglycol
 13.1% $(CH_3$-$(OCH_2H_4)$ $(OC_6H_{12})$-$OCH_3$ and $(CH_3$-$(OC_2H_4)_3$-$OCH_3$ dimethyltriglycol
 8.5% $(CH_3$-$(OC_2H_4)_2(OC_6H_{12})$-$OCH_3$ and $(CH_3$-$(OC_2H_4)_4$-$OCH_3$ dimethyltetraglycol
 4.5% $(CH_3$-$(OC_2H_4)_3(OC_6H_{12})$-$OCH_3$ and $(CH_3$-$(OC_2H_4)_5$-$OCH_3$ dimethylpentaglycol
 2.6% $(CH_3$-$(OC_2H_4)_4(OC_6H_{12})$-$OCH_3$ and $(CH_3$-$(OC_2H_4)_6$-$OCH_3$ dimethylhexaglycol.

EXAMPLE 16

1 mole of dimethylgycol and 10 g of montmorillonite of the empirical formula $Al_2O_3 . 4SiO_2 . H_2O$ are initially introduced into a 0.5 liter stirred flask fitted with a reflux condenser 0.5 mole (22 g) of ethylene oxide is then introduced as a gas in the course of 30 minutes at 50° C., whilst stirring. After the introduction of the gas has ended, the temperature is held at 50° C. for about a further 30 minutes and subsequently the mixture is analyzed.

The analysis by gas chromatography shows: 1.6% of dimethyl ether, 73.6% of dimethylglycol, 5.3% of dioxane, 0.5% of methylglycol, 13.1% of dimethyldiglycol, 1.5% of methyldiglycol, 2.6% of dimethyltriglycol, 1.5% of dimethyltetraglycol and 0.2% of dimethylpentaglycol.

EXAMPLE 17

4 moles (184 g) of dimethyl ether and 30 g of montmorillonite are initially introduced into an evacuated 1 liter stirred autoclave. 2.5 moles (231 g) of epichlorohydrin are metered in at 55° C. in the course of half an hour, whilst stirring. Subsequently the mixture is further stirred at 55° C. for another 5 hours.

After the excess dimethyl ether (90 g) has been stripped off, a residue of 360 g having the following composition, determined by gas chromatography, remains: 2.4% of dimethyl ether, 0.7% of epichlorohydrin, 75.2% of chloromethylethylene glycol dimethyl ether, 7.3% of chlormethylethylene glycol methyl ether and 15.0% of di-(chloromethylethylene glycol) dimethyl ether.

As the examples show, the reaction according to the invention can be controlled by varying the quantitative ratios of starting ether and oxacycloalkane in such a way that a particular ether compound is very predominant in the reaction mixture.

In particular, the low-molecular fractions can be continuously circulated in order to increase the build-up of reaction products of higher chain length within a homologous series.

Thus, for example, Example 2 demonstrates the following: A mixture of 1.25% of dimethyl ether, 74.35% of dimethylglycol, 1.95% of dioxane, 16.75% of dimethyldiglycol, 4.1% of dimethyltriglycol, 1.2% of dimethyltetraglycol and 0.4% of dimethylpentaglycol is obtained. Taking into account the fact that dimethylglycol and dimethyl ether can be re-used as starting ether compounds, the yield of desired homologs is 92% (16.75 + 4.1 + 1.2 + 0.4 = 22.45; 16.75 + 4.1 + 1.2 + 0.4 + 1.95 = 24.40), 68% of dimethyldiglycol being the main product.

On the other hand, Example 7 shows, for example, that the higher homologs (methylbenzyldiglycol) can be repressed by a high feed concentration of the starting ether (methyl benzyl ether). However, the relatively high quantity of recycle, thus caused, does not mean that the reaction has taken place only incompletely but it corresponds to a deliberately preselected dilution ratio in order to achieve in this way a particular distribution in the reaction product. Such measures are customary in the chemical industry. For example, in the manufacture of glycol from ethylene oxide and water, a mass ratio of 1:10, corresponding to a mole ratio of 1:24, is chosen in order to obtain a yield of ethylene glycol of 90% and to restrict the build-up of diethylene glycol and higher homologs to 10%. Accordingly, only about 4% of the water employed are consumed for the reaction. In the manufacture of ethylglycol from ethylene oxide and ethyl alcohol, alcohol excesses of 500 to 1,000% are employed in order to reduce the formation of oligomeric ethylglycols (ethyldiglycol and ethyltriglycol) to 15 to 20% (compare Ullmann, volume 8, 1974, page 205, columns 1 and 2).

EXAMPLE 18

1 mole (74 g) of diethyl ether and 0.01 mole of boron trifluoride dimethyl etherate as well as 0.82 mole (50 g) of nitromethane as a solvent are initially introduced into a 0.5 l stirred flask fitted with a reflux condenser and gas inlet tube and the mixture is warmed to 50° C.

After the catalyst has dissolved, 0.5 mole (22 g) of ethylene oxide is passed in at 50° C. in the course of 30 minutes, whilst stirring. Subsequently the mixture is stirred at 50° C. for a further 30 minutes (working up of the reaction mixture can be carried out in accordance with the procedures listed in the description and the preceding examples).

By gas chromatography, a sample of the reaction mixture shows the following analysis: 40.2% of diethyl ether, 8.3% of diethylglycol, 3.0% of dioxane, 33.8% of nitromethane, 5.7% of diethyldiglycol, 4.4% of diethyltriglycol, 2.1% of diethyltetraglycol and 1.5% of diethylphentaglycol.

EXAMPLE 19

0.5 mole (65 g) of dibutyl ether and 0.01 mole of boron trifluoride dimethyl etherate as well as 0.41 mole (25 g) of nitromethane are initially introduced into a 0.5 l stirred flask fitted with a reflux condenser and a gas inlet tube and the mixture is warmed to 50° C.

After the catalyst has dissolved, 0.25 mole (11 g) of ethylene oxide are passed in at 50° C. in the course of 30 minutes, whilst stirring. Subsequently the mixture is stirred at 50° C. for a further 30 minutes.

A sample of the reaction mixture shows the following analysis by gas chromatography: 60.1% of dibutyl ether, 2.0% of dioxane, 25.0% of nitromethane, 4.4% of dibutylglycol, 3.8% of dibutyldiglycol, 2.7% of dibutyltriglycol and 2.0% of dibutyltetraglycol.

EXAMPLE 20

1 mole (138 g) of hydroquinone dimethyl ether, 50 g of nitromethane and 0.01 mole of boron trifluoride dimethyl etherate are initially introduced into a 0.5 l stirred flask fitted with a reflux condenser. 0.5 mole (46.2 g) of epichlorohydrin is then added dropwise at 50° C. in the course of 30 minutes, whilst stirring. The mixture is then stirred at 60° C. for a further hour. The reaction mixture contains 5% of the reaction product of 1 mole of hydroquinone dimethyl ether with 1 mole of epichlorohydrin and 8% of the reaction product of 1 mole of hydroquinone dimethyl ether with 2 moles of epichlorohydrin.

We claim:

1. A process for the manufacture of chain-type ethers, in which the oxalkylene groups of oxacycloalkanes are inserted into a compound of the general formula

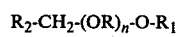

$$R_2\text{-}CH_2\text{-}(OR)_n\text{-}O\text{-}R_1 \qquad I$$

in which

R$_1$ denotes an alkyl, aryl or aralkyl radical selected from the group consisting of a straight-chain or branched alkyl radical having 1 to 12 C atoms, a phenyl radical, a phenyl radical carrying 1 to 2 chlorine atoms, a phenyl radical carrying a straight-chain or branched alkyl or alkoxy radical having 1 to 4 C atoms, a phenyl radical carrying a straight-chain or branched alkyl radical which has 1 to 4 C atoms and is substituted by 1 to 2 chlorine atoms, and an aralkyl radical composed of a phenyl radical and a straight-chain or branched alkyl radical having 1 to 4 C atoms, R$_2$ represents hydrogen, chlorine or one of the meanings of R$_1$, n is an integer from 0 to 8 and OR denotes one or more identical or different oxalkylene groups selected from the group consisting of:

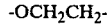
-OCH$_2$CH$_2$-

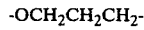
-OCH$_2$CH$_2$CH$_2$-

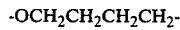
-OCH$_2$CH$_2$CH$_2$CH$_2$-

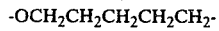
-OCH$_2$CH$_2$CH$_2$CH$_2$CH$_2$-

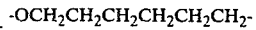
-OCH$_2$CH$_2$CH$_2$CH$_2$CH$_2$CH$_2$-

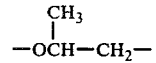

$$\begin{array}{c} \text{CH}_3 \\ | \\ -\text{OCH}-\text{CH}_2- \end{array}$$

-continued

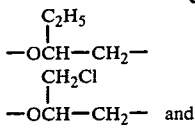

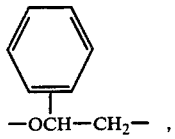

wherein the compounds according to the formula I are reacted, in the presence of Lewis acids in an amount of 0.01 mole % to 10 mole %, relative to the compound of the formula I, and at a temperature from 20 to 90° C., with oxacylcloalkanes selected from the group consisting of ethylene oxide, 1,2-propylene oxide, 1,2-butylene oxide, trimethylene oxide, tetramethylene oxide, pentamethylene oxide, hexamethylene oxide, epichlorohydrin and styrene oxide, individually or as mixtures with one another, 3-membered to 4-membered oxacycloalkanes also being present in an amount from at least 5% by weight, relative to the total mixture of oxacycloalkane in the case of a reaction with oxacycloalkanes having more than 4 members.

2. A process as claimed in claim 1, wherein the 3-membered to 4-membered oxacycloalkane is employed in an amount from 10 to 90% by weight, relative to the total mixture of oxacacloalkane in the case of a reaction with oxacycloalkanes having more than 4 members.

3. A process as claimed in claim 1, wherein the compounds according to formula I, employed are those in which $R_1$ denotes a straight-chain alkyl radical having 1 to 4 C atoms, a phenyl radical, a phenyl radical carrying 1 to 2 chlorine atoms or a benzyl radical, OR represents one or several different radicals out of those which follow:

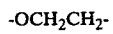

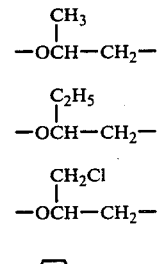

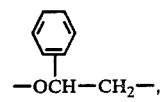

the oxacycloalkanes employed are ethylene oxide, 1,2-propylene oxide, 1,2-butylene oxide, tetramethylene oxide, epichlorohydrin and styrene oxide, individually or as a mixture with one another, and the Lewis acids employed are those from the group comprising the metal halides and metalloid halides, the hydrogen acids, the aluminum hydrosilicates, the coordination complexes of metal halides or metalloid halides with halogenoalkyls, ethers, acid chlorides, acid esters or acid anhydrides, the trialkyloxonium salt complexes, the acylium salt complexes and from the group of the unsaturated tertiary oxonium salts.

* * * * *